United States Patent [19]

Maarschalkerweerd

[11] Patent Number: 4,872,980

[45] Date of Patent: Oct. 10, 1989

[54] FLUID PURIFICATION DEVICE

[75] Inventor: Jan Maarschalkerweerd, Lambeth, Canada

[73] Assignee: Trojan Technologies, Inc., Canada

[21] Appl. No.: 243,845

[22] Filed: Sep. 13, 1988

[51] Int. Cl.⁴ ............................................ G01N 21/01
[52] U.S. Cl. .................................. 210/243; 210/192; 250/436; 250/435; 422/24
[58] Field of Search ................... 210/748, 243, 192; 250/432 R, 435, 436, 428; 422/24

[56] References Cited

U.S. PATENT DOCUMENTS

| | | | |
|---|---|---|---|
| 3,462,597 | 8/1969 | Young | 250/43 |
| 4,255,663 | 3/1981 | Lewis | 250/436 |
| 4,367,410 | 1/1983 | Wood | 250/431 |
| 4,400,270 | 8/1983 | Hillman | 210/103 |
| 4,482,809 | 11/1984 | Maarschalkerweerd | 250/435 |
| 4,757,205 | 7/1988 | Latel et al. | 250/435 |

Primary Examiner—W. Gary Jones
Assistant Examiner—Matthew O. Savage
Attorney, Agent, or Firm—William E. Mouzavires

[57] ABSTRACT

A fluid purification device including an inverted U-shape frame whose legs support a plurality of lamp assemblies each including an ultraviolet lamp received in a protective sleeve. One of the legs is hollow and receives lead wires connected to the lamps through openings spaced along the leg. The protective sleeves at one of their ends are resiliently mounted to the hollow leg at the openings, and seals are provided to prevent fluid from entering into the hollow leg and the protective sleeve. The other ends of the protective sleeves are closed and held in receptacles in the other frame leg which is formed by two plates fixed to each other. "O" rings provided along the other leg receive the protective sleeves to provide flexible seats. An electrical ballast controlling voltage and amperage at the lamps is incorporated in the frame.

35 Claims, 2 Drawing Sheets

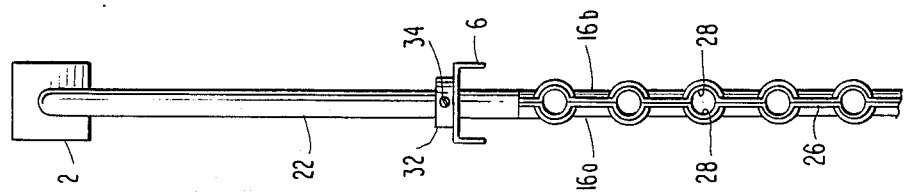
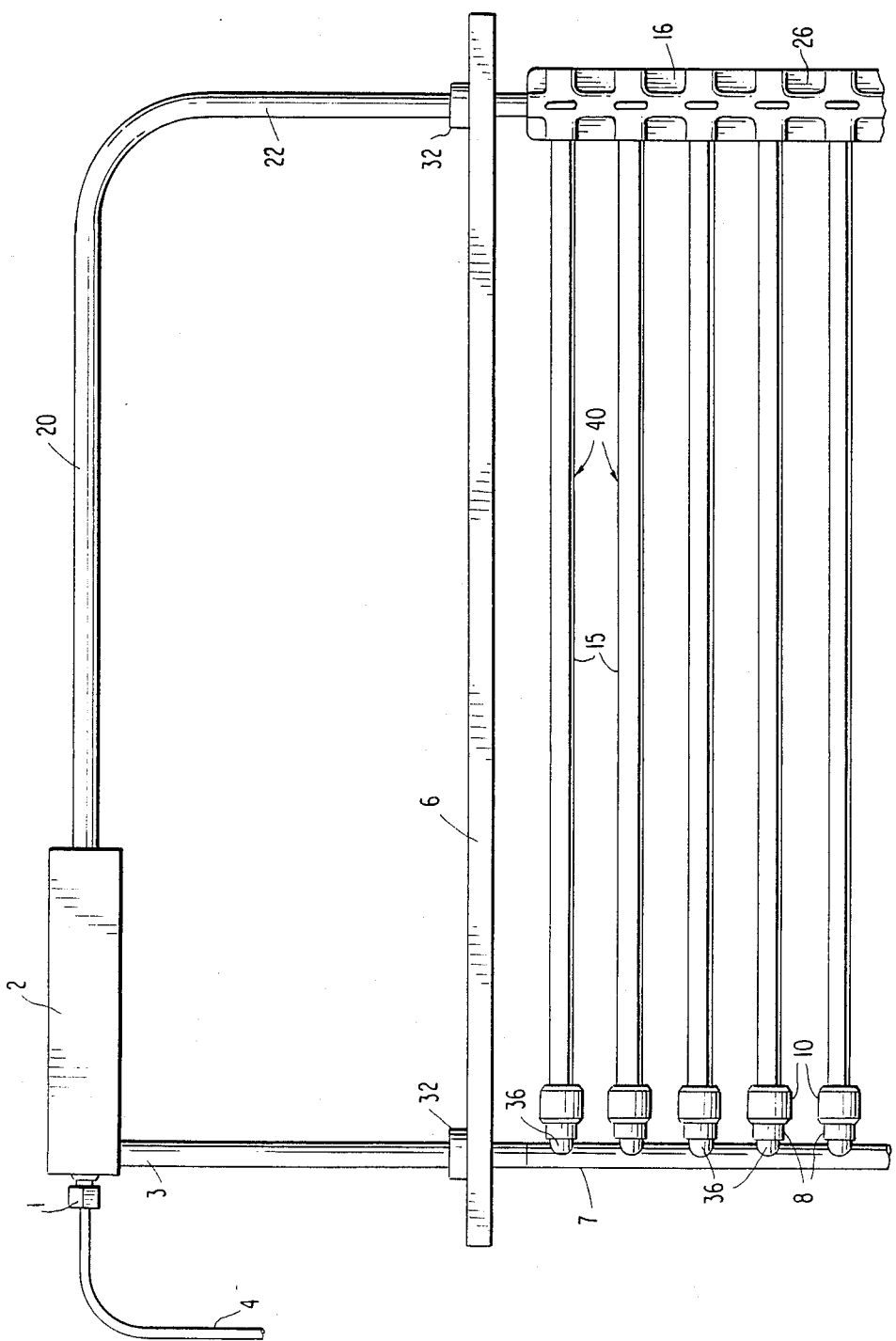

FLUID PURIFICATION DEVICE

BACKGROUND OF THE INVENTION

The present invention relates to purification or sterilization of fluids, such as waste water, through ultraviolet light rays which are capable of killing or destroying unwanted microorganisms in fluids as is well-known. More specifically, the present invention relates to ultraviolet lamp systems which are immersed in the fluid to be purified. The systems may include a plurality of lamp modules each containing a plurality of lamp assemblies supported in parallel by and between spaced vertical legs forming a part of the module frame such as, for example, disclosed in U.S. Pat. No. 4,482,809 assigned by the inventor herein to the same assignee of the subject application. In the module device of this patent, the ultraviolet lamps are mounted to the legs of the frame by their surrounding protective sleeves whose opposite ends are open and mounted and sealed in sockets spaced along the legs. The lamps are powered through lead wires extending from an external control panel and received in both legs of the frame which are hollow for this purpose. The lead wires are connected to opposite ends of the lamps through contacts in the sockets; there being a separate pair of lead wires connected to each lamp at the opposite ends thereof respectively. The voltage and amperage of the lamps are contolled at a control panel located externally of the lamp modules.

OBJECTS OF THE PRESENT INVENTION

An object of the present invention is to provide certain improvements in fluid purification devices of the type shown, for example, in U.S. Pat. No. 4,482,809 mentioned above. Included herein is the provision of a fluid purification device of the type described which simplifies and improves the mounting and sealing of the lamp assemblies while simplifying and reducing the electrical connections for the lamps. Additionally included is the provision of such a device having an improved frame which is more economical to manufacture and facilitates assembly of the lamp units. Another object is to provide such a fluid purification device incorporating in its own frame, an electrical ballast for controlling the voltage and amperage through the lamps.

SUMMARY OF INVENTION

A preferred embodiment of the device of the present invention includes a frame having spaced legs in which a plurality of lamp assemblies are mounted; each assembly including an elongated ultraviolet lamp and a surrounding protective sleeve closed at one end. One of the legs has a hollow passage receiving lead wires for powering all of the lamps and the other leg is free of any lead wires. The lead wires are connected to one of the ends of the lamps through openings spaced along the hollow leg. One of the ends of the protective sleeves is open and mounted in an improved manner to the hollow legs in alignment with the leg openings which are sealed by closures containing electrical conductors interconnecting the lead wires and the lamps. The inner and outer surfaces of the protective sleeves at said one end thereof are sealed to prevent fluid contact with the electrical connections.

The other ends of the protective sleeves are closed and mounted in resilient seats carried in receptacles formed in the other frame leg. The latter is formed by two plates fixed together with registering recesses forming the receptacles. An electrical ballast for controlling the voltage and amperage at the lamps is incorporated in the frame of the device.

DRAWINGS

Other objects and advantages of the present invention will become apparent from the following more detailed description taken in conjunction with the attached drawings in which:

FIG. 1 is a side elevational view of a water purifying device constituting a preferred embodiment of the present invention;

FIG. 4 is an end elevational view of the device.

DETAILED DESCRIPTION

Figure 2:
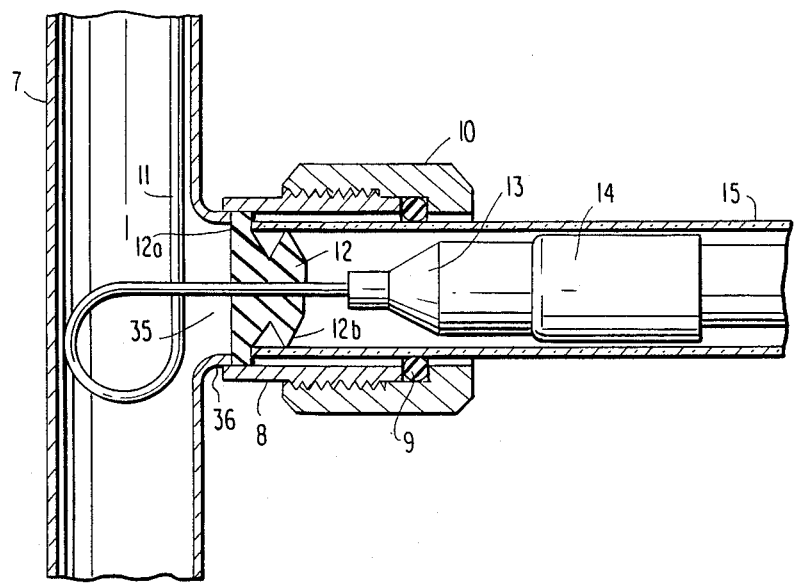
FIG. 2 is an enlarged, fragmental, cross-sectional view of an end portion of the device where a lamp assembly is mounted in the frame of the device.

Referring to the drawings in detail there is shown for illustrative purposes only, a fluid purification device constituting a preferred embodiment of the invention. The device is a module to be used with other similar or identical modules for purifying fluids such as waste water with ultraviolet rays according to purification principles which are well-known and need not be described here. Referring to FIG. 1, the device in its preferred form, includes an inverted U-shape frame including opposite legs interconnected at the top by a cross piece 20 which includes a ballast 2 connected to a power cord 4 by a strain relief 1. Ballast 2 controls the voltage and amperage through ultraviolet lamps 14 mounted to and between the frame legs as will be described below. To initially energize the lamps 14, high voltage on the order of 600 volts at the ballast is required but once the lamps are energized, a lower voltage, for example, 180 volts at the ballast is sufficient and this variation of the voltage is provided by the ballast. Ballast 2 also functions to limit the amperage through the lamps.

The frame leg on the left as shown in FIG. 1 includes upper and lower hollow tubular sections 3 and 7 joined, such as by butt welding, to each other in axial alignment, with the lower end of section 7 being closed. The frame leg shown on the right in FIG. 1 is also formed in two joined sections including an upper section 22 which may be integral with cross piece 20 and a lower section 16 formed by two plates 16a and 16b. The latter are welded together at flat web portions 26 and are formed with registering semi-cylindrical recesses 28 providing cylindrical receptacles 30 extending transversely between the webs for receiving the lamp assemblies as will be described below. Mounted to and between intermediate portions of the frame legs is an inverted generally U-shaped channel 6 having collars 32 fixed thereto with set screws 34 for securing channel 6 in desired position. Channel 6 serves to reinforce the frame and also as a barrier to the ultraviolet light.

Lower leg section 7 has a plurality of openings 35 formed along its length at spaced locations. The lamp assemblies are mounted at one of their ends to leg 7 in alignment with openings 35 respectively. In the preferred embodiment, cylindrical mounting flanges or flares 36 are fixed to or formed with the leg section 7 about the openings 35, and fixed about each of the mounting flanges 36, such as by welding, is a cylindrical mounting sleeve 8. The lamp assemblies, generally designated 40 in FIG. 1, are mounted at their opposite ends in mounting sleeves 8 and receptacles 30 respectively.

Figure 3:
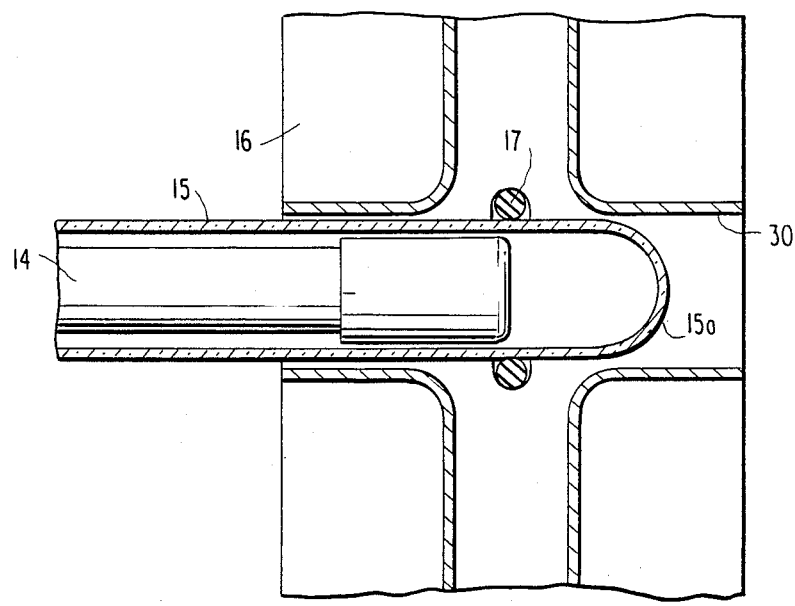
FIG. 3 is a view generally similar to FIG. 2 but taken at an opposite end portion of the device.

Each lamp assembly 40 includes an elongated ultraviolet lamp 14 and an elongated protective quartz sleeve 15 surrounding the lamp 14 to fully enclose the same. In the preferred embodiment, the right end of the protective sleeve 15, as shown in FIG. 1, extends beyond the adjacent end of lamp 14 and is closed at 15a (see FIG. 3). The left end of protective sleeve 15 extends beyond the adjacent end of lamp 14 and is formed with an opening in alignment with the opening 35. The left end of the protective sleeve 15 is mounted coaxially within the mounting sleeve 8 while the right end is mounted in receptacle 30 as best shown in FIG. 3. In order to prevent breakage of the protective sleeve at its right end portion, a plurality of flexible and resilient seats, preferably "O" rings 17 are provided in the split leg section to surround the receptacles 30 and receive the protective sleeves respectively as shown in FIG. 3.

In the preferred embodiment shown, each lamp 14 has, on the left end thereof as shown, a connector 13 having contact pins (not shown) received in sockets formed in the end of the lamp. Lead wires 11 provided for driving the lamps respectively extend from the connectors 13 through openings 35 and vertically within the hollow passages of leg sections 3 and 7. All of the lead wires 11 for driving all of the lamps 14 of each module are located in the left-hand leg sections 3 and 7 from which they are connected to the ballast 2.

In order to seal the space between the mounting sleeve 8 and the protective sleeve 15, an annular seal, preferably an "O" ring 9, is mounted about each protective sleeve 15 at the end of the mounting sleeve 8. A nut 10 is threaded onto mounting sleeve 8 and has an internal shoulder engaged with the "O" ring 9. Advancement of nut 10 along mounting sleeve 8 will deform the "O" ring radially inwardly to establish a fluid tight seal about the protective sleeve 8. "O" rings 9 also help to provide a resilient mount for the lamp assemblies.

In order to prevent entry of fluid through openings 35 and into the hollow leg section 7, each of the openings 35 is sealed closed by a closure or plug 12 made of a suitable flexible rubberlike material. In the preferred embodiment shown in FIG. 2, closure 12 includes a first sealing segment 12a having a generally cylindrical shape and butted against the flanges 36 surrounding openings 35 with the peripheral surface of the sealing segment 12a continuously in sealing engagement with the inside surface of the mounting sleeve 8 as shown in FIG. 2. For added insurance, closure 12 is formed with another sealing segment 12b axially spaced inwardly of segment 12a and formed by opposed frusto-conical portions defining a thin circular sealing lip in continuous sealing engagement with the inside surface of the protective sleeve 15; it being understood that the diameter of sealing segment 12b is less than that of segment 12a. Closure 12 also provides a flexible and resilient cushion mount for the end of the protective sleeve 15 which abuts against the sealing segment 12a while being received on sealing segment 12b as shown in FIG. 2. It will thus be seen that should the protective sleeve 15 break allowing fluid to pass "O" ring 9, the fluid will be prevented from passing sealing segments 12a or 12b to enter the leg 7.

In the preferred embodiment shown, the closures 12 are molded about a respective lead wire 11 which extends inwardly from the closure 12 to the connector 13. However, in other embodiments not shown, the connector 13 may be formed or located within the closure 12 itself which may be an electrical receptacle. Additionally, other types of electrical connections to the lamps 14 may be made at or in the closure 12.

The various parts of the module frame including split leg sections 16a, 16b may be made from suitable non-corrosive material such as stainless steel. Also, if desired, nuts 10 may be made from plastic such as DELRIN material.

It will be understood that although only one module has been shown and described, in use a typical installation at a fluid purification site, will include a plurality of modules arranged such as shown in U.S. Pat. No. 4,482,809, reference to which is hereby made for disclosure purposes.

It will thus be seen that the present invention reduces the number of external lead wires required for the lamps while also placing them in a single frame leg thus allowing the other leg to be economically made and without electrical connections and seals at that leg. In addition, the incorporation of the ballast in the frame itself obviates the need of an external control panel to further reduce parts and cost. Moreover, the present invention improves the mounting and sealing of the lamp assemblies while, at the same time, preventing fluid contact with the lead wires and electrical connections.

What is claimed is:

1. A fluid purification device comprising in combination a frame including a pair of opposed legs laterally spaced from each other, one of said legs having a longitudinally extending passage therein, a plurality of water purification lamp assemblies extending between and supported by said legs, each lamp assembly having one end thereof located towards said one leg and an opposite end located towards the other leg, a plurality of electrical lead wires located in said passage in said one leg and respectively connected to said lamp assemblies at said one end thereof, said one leg having a plurality of openings spaced along said one leg, a plurality of first seals surrounding said lead wires and respectively sealing said openings from the fluid, electrical connector means connecting said lead wires to said lamp assemblies respectively while being sealed to prevent contact with fluid surrounding said lamp assemblies when in use, and wherein said other leg is free of any lead wires.

2. The device defined in claim 1 wherein said lamp assemblies include a plurality of lamps and protective sleeves surrounding and enclosing the lamps respectively, said protective sleeves having openings in one end thereof located adjacent said openings in said one leg and having opposite closed ends supported in said other leg, said one end of said protective sleeves being in sealing engagement with said first seals respectively to close said openings in said protective sleeves.

3. The device defined in claim 2 further including a plurality of second seals respectively located in said openings of said protective sleeves outwardly of said lamps to seal said openings in said protective sleeves.

4. The device defined in claim 3 including a plurality of mounting sleeves respectively fixed about said openings in said one leg while receiving portions of said protective sleeves adjacent said one leg, said mounting sleeves each being sealed about an outer surface of an associated protective sleeve.

5. The device defined in claim 4 wherein each mounting sleeve has associated therewith means including an "O" ring sealing one end of the mounting sleeve about the associated protective sleeve.

6. The device defined in claim 5 wherein said mounting sleeves respectively receive said first seals in sealing engagement therewith.

7. The device defined in claim 5 further including a plurality of nuts respectively engaged about said mounting sleeves to urge said "O" rings in sealing engagement about said protective sleeves.

8. The device defined in claim 3 wherein said second seals are integral with said first seals.

9. The device defined in claim 2 wherein said other leg of said frame includes two longitudinally split plate sections including registered recesses forming receptacles respectively receiving said opposite closed ends of said protective sleeves.

10. The device defined in claim 9 including a plurality of annular flexible seats mounted in and at spaced locations along said split plate sections and respectively receiving said opposite closed ends of said protective sleeves.

11. The device defined in claim 1 wherein said other leg of said frame includes two longitudinally split plate sections including registered recesses forming receptacles respectively receiving said opposite ends of said lamps.

12. The device defined in claim 11 including a ballast incorporated in the frame for controlling the voltage and amperage through said lamps.

13. The device defined in claim 1 including a ballast incorporated in the frame for controlling the voltage and amperage through said lamps.

14. The device defined in claim 1 wherein said electrical conductor means are integral with said lead wires.

15. The device defined in claim 14 wherein said first seals are molded about said lead wires.

16. The device defined in claim 1 including a plurality of protective sleeves surrounding and enclosing said lamps respectively, said protective sleeves having first ends mounted about said first seals respectively in sealing engagement therewith and having opposite closed ends respectively mounted in said other leg.

17. A fluid purification device comprising in combination, a frame including a pair of legs laterally spaced from each other, at least one lamp assembly extending between and supported by said legs, said lamp assembly including a lamp and a protective sleeve surrounding the lamp throughout the length thereof, one of said legs having a passage extending longitudinally therein, an electrical lead wire located in said passage to be connected with said lamp respectively, said one leg further having an opening spaced along the length thereof in general alignment with the lamp assembly and communicating with said passage, a closure sealing said opening and surrounding said lead wires, and having an electrical connector means interconnecting the lead wire and lamp, and wherein said protective sleeve has an open end mounted about said closure and an opposite end supported by the other leg of the frame and sealed about the lamp.

18. The device defined in claim 17 further including a mounting sleeve fixed to said one leg about said opening while receiving said closure and said protective sleeve, and an annular seal in sealing engagement between said mounting sleeve and said protective sleeve.

19. The device defined in claim 18 wherein said mounting sleeve is engaged about said closure and sealed thereby.

20. The device defined in claim 18 wherein said closure has a first annular portion sealingly engaged against an internal surface of the mounting sleeve and a second annular portion sealingly engaged against an internal surface of the protective sleeve outwardly of the lamp.

21. The device defined in claim 17 wherein said other end of said protective sleeve is closed and supported on said other leg.

22. The device defined in claim 21 wherein said other leg of the frame includes two split sections having registering recesses forming a receptacle receiving the closed end of said protective sleeve.

23. The device defined in claim 22 including a ballast incorporated in said frame for controlling the voltage and amperage in the lamp.

24. The device defined in claim 17 including a ballast incorporated in said frame for controlling the voltage and amperage in the lamp.

25. A fluid purification device comprising in combination, a frame including a pair of opposed legs laterally spaced from each other, one of said legs having a longitudinally extending passage therein, a plurality of water purification lamps extending between and supported by said legs, each lamp having one end thereof located towards said one leg and an opposite end located towards the other leg, a plurality of electrical lead wires located in said passage and respectively connected to said lamps at said one end thereof, said one leg having a plurality of openings spaced along said one leg for connecting said lead wires to said lamps and a plurality of protective sleeves respectively surrounding said lamps, each of said protective sleeves having an open end, means mounting and sealing the open end of each protective sleeve to said one leg in alignment with one of said openings in said one leg, each of said protective sleeves having a closed end opposite the open end thereof mounted to said other leg and wherein said other leg is free of any lead wires.

26. The device defined in claim 25 wherein said other leg of said frame includes two longitudinally split sections including registered recesses forming receptacles respectively receiving said closed ends of said protective sleeves.

27. The device defined in claim 25 including a ballast incorporated in said frame for controlling the voltage and amperage in said lamps.

28. A fluid purification device comprising in combination a frame including a pair of legs laterally spaced from each other, a plurality of lamp assemblies extending between and supported by said legs at respective locations spaced along the legs, said lamp assemblies each including an elongated lamp and a surrounding protective sleeve, one of said legs including a pair of elongated plates fixed together and having transversely extending recesses in registry with each other to form a plurality of receptacles along said one leg respectively receiving one of the ends of said protective sleeves, and means associated with said other leg for powering said lamps.

29. The device defined in claim 28 further including a plurality of flexible annular seats mounted in said plates and about said receptacles and receiving said protective sleeves respectively.

30. The device defined in claim 28 wherein the other leg has a plurality of openings spaced along the length thereof in general alignment with said lamp assemblies, means mounting and sealing the other ends of said protective sleeves to said other leg in alignment with said openings in said other leg, said other leg having a longitudinal passage therein in communication with said openings in said other leg, and a plurality of conductors extending through said passage for driving all of said lamps.

31. The device defined in claim 30 including a ballast incorporated in the frame and connected to said lead wires to control the voltage and amperage in said lamps.

32. A fluid purification device comprising in combination a frame including a pair of opposed legs laterally spaced from each other, a plurality of water purification lamp assemblies extending between and supported by said legs, each lamp assembly having one end thereof located towards one of said legs and an opposite end which is closed and located towards the other leg, a plurality of electrical lead wires respectively connected to said lamp assemblies and a ballast incorporated in said frame and including means connected to said lead wires for controlling said lamps and wherein said one leg has a longitudinal passage receiving said lead wires.

33. The device defined in claim 32 wherein said other leg of said frame includes two longitudinally split sections including registered recesses forming receptacles respectively receiving said opposite ends of said lamps.

34. A fluid purification device comprising in combination, a frame including a pair of opposed legs laterally spaced from each other, one of said legs having a longitudinally extending passage therein, a water purification lamp extending between and supported by said legs, said lamp having one end thereof located towards said one leg and an opposite end located towards the other leg, an electrical lead wire located in said passage and connected to said lamp at said one end thereof, said one leg having an opening in said one leg for connecting said lead wire to said lamp and a protective sleeve surrounding said lamp, said protective sleeve having an open end and a seal sealing the open end, means mounting the open end with respect to the fluid of said protective sleeve to said one leg, said protective sleeve having a closed end opposite the open end thereof mounted to said other leg and wherein said other leg is free of any lead wires.

35. A fluid purification device comprising in combination a frame including a pair of legs laterally spaced from each other, a lamp assembly extending between and supported by said legs at a location along the legs, said lamp assembly including an elongated lamp and a surrounding protective sleeve, one of said legs including a pair of elongated plates fixed together and having transversely extending recesses in registry with each other to form a receptacle along said one leg receiving one of the ends of said protective sleeve and means associated with the other leg for conveying electricity to the lamp.

* * * * *

UNITED STATES PATENT AND TRADEMARK OFFICE
CERTIFICATE OF CORRECTION

PATENT NO. : 4,872,980

DATED : October 10, 1989

INVENTOR(S) : JAN MAARSCHALKERWEERD

It is certified that error appears in the above-identified patent and that said Letters Patent is hereby corrected as shown below:

Column 5, line 34, delete "conductor" and insert -- connector --.

Column 8, line 10, after "end" (second occurrence), insert -- with respect to the fluid --;

line 11, after "end" delete "with respect to the fluid".

Signed and Sealed this

Twenty-seventh Day of September, 1994

Attest:

BRUCE LEHMAN

*Attesting Officer*     *Commissioner of Patents and Trademarks*